United States Patent
Vempada et al.

(10) Patent No.: US 9,536,145 B2
(45) Date of Patent: Jan. 3, 2017

(54) SYSTEM AND METHOD FOR SELECTING FEATURES FOR IDENTIFYING HUMAN ACTIVITIES IN A HUMAN-COMPUTER INTERACTING ENVIRONMENT

(71) Applicant: Tata Consultancy Services Limited, Maharashtra (IN)

(72) Inventors: Ramu Reddy Vempada, Kolkata (IN); Tanushyam Chattopadhyay, Kolkata (IN)

(73) Assignee: TATA CONSULTANCY SERVICES LIMITED, Mumbai, Maharashtra (IN)

( * ) Notice: Subject to any disclaimer, the term of this patent is extended or adjusted under 35 U.S.C. 154(b) by 0 days.

(21) Appl. No.: 14/576,627

(22) Filed: Dec. 19, 2014

(65) Prior Publication Data

US 2015/0186724 A1     Jul. 2, 2015

(30) Foreign Application Priority Data

Dec. 27, 2013   (IN) .................. 4097/MUM/2013

(51) Int. Cl.
*G06K 9/00*    (2006.01)
*A61B 5/11*    (2006.01)
(Continued)

(52) U.S. Cl.
CPC ......... *G06K 9/00624* (2013.01); *A61B 5/1123* (2013.01); *A61B 5/1128* (2013.01); *A61B 5/7267* (2013.01); *G06F 3/017* (2013.01); *G06K 9/00342* (2013.01); *G06K 9/00348* (2013.01); *G06K 9/44* (2013.01); *G06K 9/52* (2013.01); *G06K 9/6269* (2013.01)

(58) Field of Classification Search
None
See application file for complete search history.

(56) References Cited

U.S. PATENT DOCUMENTS 6,256,033 B1 *  7/2001  Nguyen ............... G06F 3/017
                                                   345/156
7,602,301 B1 * 10/2009  Stirling ............ A61B 5/1127
                                                   340/573.1

(Continued)

FOREIGN PATENT DOCUMENTS

EP      2538372 A1   12/2012
WO   2013027091 A1    2/2013

OTHER PUBLICATIONS

Ofli et al."Sequence of the Most Informative Joints (SMIJ): A New Representation for Human Skeletal Action Recognition", 2012 IEEE, pp. 8-13.*

(Continued)

Primary Examiner — Jason Heidemann
(74) Attorney, Agent, or Firm — Thompson Hine LLP

(57) ABSTRACT

A System and method for identifying one or more human activities in a human-computer interacting environment. Skeleton points associated with a human are received. A data variation factor for the skeleton points is calculated, and a set of skeleton points is selected based on the data variation factor. One or more features are defined from the set of skeleton points by identifying a variance in coordinates of the set of skeleton points by using one or more statistical parameters. The one or more features are used to identify the one or more human activities.

13 Claims, 5 Drawing Sheets

(51) Int. Cl.
*G06F 3/01* (2006.01)
*G06K 9/52* (2006.01)
*A61B 5/00* (2006.01)
*G06K 9/44* (2006.01)
*G06K 9/62* (2006.01)

(56) References Cited

U.S. PATENT DOCUMENTS

| | | | |
|---|---|---|---|
| 8,204,311 B2 | 6/2012 | Kim et al. | |
| 8,786,680 B2 * | 7/2014 | Shiratori | G06F 3/011 345/156 |
| 2004/0193413 A1 * | 9/2004 | Wilson | G06F 3/017 704/243 |
| 2006/0274947 A1 * | 12/2006 | Fujimura | G06K 9/00362 382/201 |
| 2008/0223131 A1 * | 9/2008 | Vannucci | A61B 5/112 73/510 |
| 2009/0175540 A1 | 7/2009 | Dariush et al. | |
| 2009/0298650 A1 * | 12/2009 | Kutliroff | A63B 71/0622 482/8 |
| 2009/0316983 A1 * | 12/2009 | Han | G06K 9/00342 382/159 |
| 2010/0164862 A1 * | 7/2010 | Sullivan | G06K 9/3216 345/156 |
| 2010/0197390 A1 * | 8/2010 | Craig | G06K 9/00369 463/30 |
| 2010/0208038 A1 * | 8/2010 | Kutliroff | G06K 9/00201 348/46 |
| 2010/0306712 A1 * | 12/2010 | Snook | G06K 9/00342 715/863 |
| 2011/0111798 A1 * | 5/2011 | Jeon | G06F 3/017 455/556.1 |
| 2011/0169726 A1 * | 7/2011 | Holmdahl | G06K 9/00342 345/156 |
| 2011/0268320 A1 * | 11/2011 | Huang | G06K 9/00718 382/103 |
| 2011/0317871 A1 | 12/2011 | Tossell et al. | |
| 2012/0056800 A1 * | 3/2012 | Williams | G06F 3/011 345/156 |
| 2012/0159290 A1 * | 6/2012 | Pulsipher | G06K 9/00369 714/819 |
| 2013/0101170 A1 * | 4/2013 | Park | G06T 7/0079 382/103 |
| 2013/0272571 A1 | 10/2013 | Qu et al. | |
| 2013/0278501 A1 | 10/2013 | Bulzacki | |
| 2013/0322720 A1 * | 12/2013 | Hu | G06T 15/00 382/131 |
| 2014/0119640 A1 * | 5/2014 | Craig | G06F 3/011 382/159 |
| 2014/0198954 A1 * | 7/2014 | Bulzacki | G06K 9/00342 382/103 |
| 2014/0334670 A1 * | 11/2014 | Guigues | G06T 7/2046 382/103 |

OTHER PUBLICATIONS

Stack Overflow Forum—KNN algo in matlab, last updated Jun. 3, 2012, accessed on Jun. 7, 2016, http://stackoverflow.com/questions/10855461/knn-algo-in-matlab.*

Computer Vision and System Laboratory; "Skeleton-Based Segmentation and Recognition of Human Activities from Video Sequences" 2004.

* cited by examiner

SYSTEM AND METHOD FOR SELECTING FEATURES FOR IDENTIFYING HUMAN ACTIVITIES IN A HUMAN-COMPUTER INTERACTING ENVIRONMENT

CROSS-REFERENCE TO RELATED APPLICATIONS AND PRIORITY

The present application does claim priority from the Indian patent application 4097/MUM/2013 filed on 27 Dec., 2013.

TECHNICAL FIELD

The present disclosure in general relates to method(s) and system(s) for identifying human activity. More particularly, the present disclosure relates to method(s) and system(s) for selecting features to identify human activity in a human-computer interacting environment.

BACKGROUND

Monitoring daily life activities has become very important for conducting human surveys. Computer-based interactive systems and varieties of sensors are widely used to monitor human activities like sitting, walking, and standing. Mobile phones with embedded sensors may also be used for monitoring and analyzing human activities.

Use of mobile phones has been considered a user-friendly approach. However, to monitor activities through a mobile phone, one should carry the mobile phone all the time. In most of the cases like watching TV or while sleeping, there is a possibility that one may forget to carry the mobile phone. Further, ubiquitous sensors are often considered uncomfortable and are difficult to deploy. Also, camera based systems are not preferred due to issues of privacy.

Therefore, the best approach is the use of computer vision technology to sense and monitor human activities by using skeleton joints. However, in computer vision technology, many of the skeleton joints are sensitive to noise. Further, skeleton-based methods are considered expensive.

SUMMARY OF THE INVENTION

This summary is provided to introduce aspects related to system(s) and method(s) for selecting features for identifying human activities in a human-computer interacting environment, and the aspects are further described below in the detailed description. This summary is not intended to identify essential features of the claimed subject matter, nor is it intended for use in determining or limiting the scope of the claimed subject matter.

The present disclosure relates to a system for selecting one or more features to identify one or more human activities in a human-computer interacting environment. The system includes a processor and a non-transitory memory coupled to the processor. The processor is capable of executing a plurality of modules stored in the memory. The plurality of modules includes a receiving module configured to receive skeleton points associated with one or more humans, where the one or more humans performs the one or more human activities, and wherein the skeleton points include a plurality of position coordinates of the one or more humans, and a computation module configured to calculate a data variation factor for the skeleton points, where the data variation factor identifies a variation between at least two of the plurality of position coordinates of the one or more humans. The plurality of modules comprises a selection module configured to select a set of skeleton points from the skeleton points based on the data variation factor and a feature defining module. The feature defining module is configured to identify a change in position co-ordinates associated with the set of skeleton points by using one or more statistical parameters, where the set of skeleton points defines the one or more human activities to be identified and extracts one or more features from the set of skeleton points based on the change in the position coordinates. The plurality of modules includes an identification module configured to use the one or more features in order to identify the one or more human activities.

The present disclosure also relates to a method for selecting one or more features to identify one or more human activities in a human-computer interacting environment. The method includes receiving skeleton points associated with one or more humans, where the one or more humans performs the one or more human activities, and where the skeleton points include position coordinates of the one or more humans, calculating a data variation factor for the skeleton points, where the data variation factor identifies a variation between the position coordinates of the one or more humans, and selecting a set of skeleton points from the skeleton points based on the data variation factor. The method includes identifying a change in position coordinates associated with the set of skeleton points by using one or more statistical parameters, where the set of skeleton points defines one or more human activity to be identified, extracting one or more features from the set of skeleton points based on the change in the position coordinates, and identifying the one or more human activities by using the one or more features.

The present disclosure also relates to a computer program product having embodied thereon a computer program for selecting one or more features to identify one or more human activities in a human-computer interacting environment, the computer program product including a program code for receiving skeleton points associated with one or more human, where the one or more human performs the one or more human activities, and where the skeleton points comprise position coordinates of the one or more humans, a program code for calculating a data variation factor for the skeleton points, where the data variation factor identifies a variation between the position coordinates of one or more humans, and a program code for selecting a set of skeleton points from the skeleton points based on the data variation factor. The computer program product includes a program code for identifying a change in position co-ordinates associated with the set of skeleton points by using one or more statistical parameters, where the set of skeleton points defines one or more human activity to be identified, a program code for extracting one or more features from the set of skeleton points based on the change in the position coordinates, and a program code for identifying the one or more human activities by using the one or more features.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

While aspects of the described system and method for selecting features for identifying human activities in a human-computer interacting environment may be implemented in any number of different computing systems, environments, and/or configurations, the embodiments are described in the context of the following exemplary system.

Figure 1:
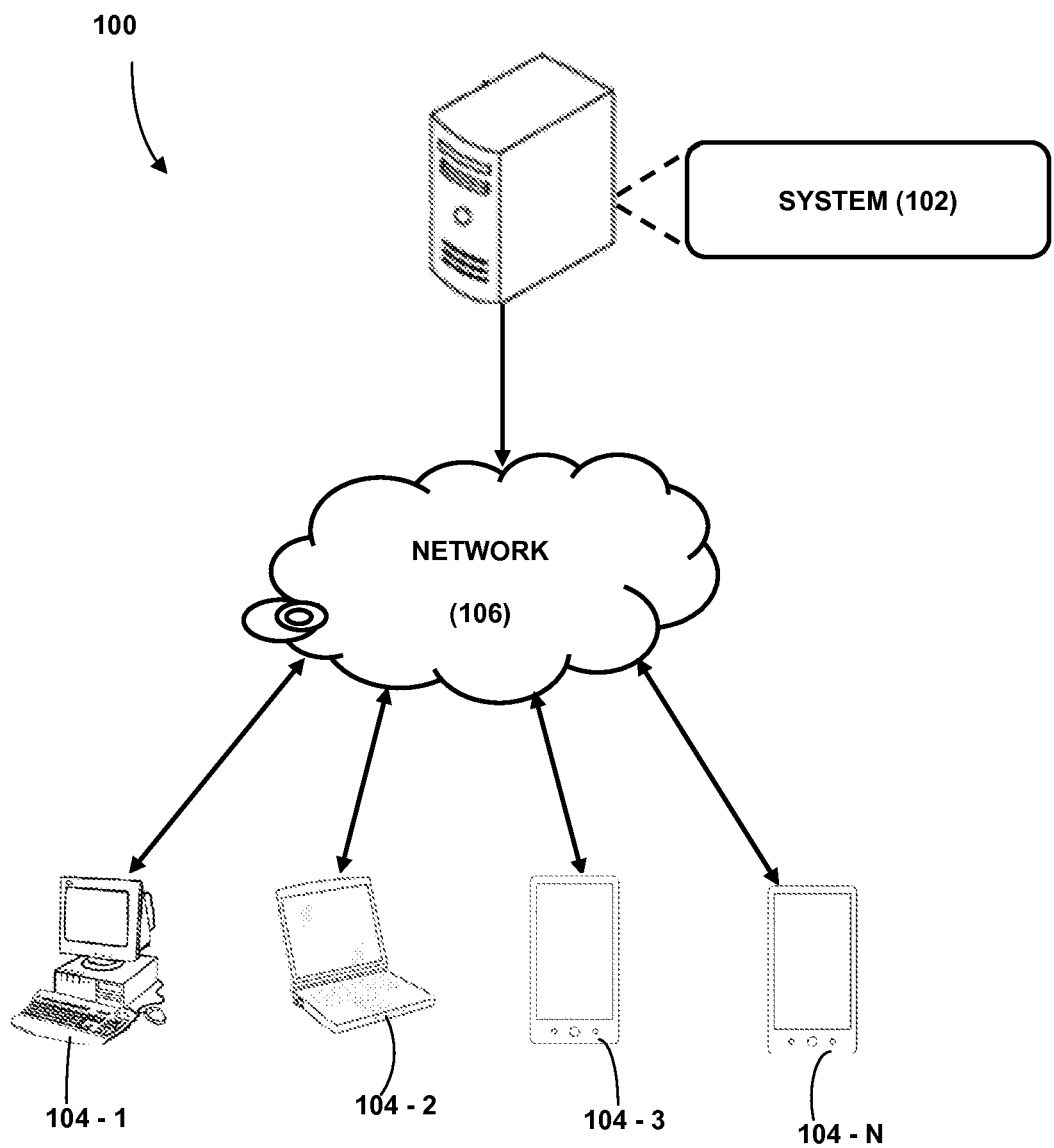
FIG. 1 illustrates a network implementation of a system for selecting features for identifying human activities in a human-computer interacting environment, in accordance with an embodiment of the present subject matter.

Referring now to FIG. 1, a network implementation 100 of system 102 for selecting features for identifying human activities in a human-computer interacting environment is shown. Skeleton points are received. Skeleton points are pre-sensed by using one or more sensors. A data variation factor is calculated to determine a variation between one or more humans while performing the human activities and a variation between the human activities. A set of skeleton points are selected from the skeleton points. The set of skeleton points is further processed and one or more features are identified. The one or more features are then used to identify the human activities.

Although the present subject matter is explained considering that the system 102 is implemented as an application on a server, it may be understood that the system 102 may also be implemented in a variety of computing systems, such as a laptop computer, a desktop computer, a notebook, a workstation, a mainframe computer, a server, a network server, and the like. In one implementation, the system 102 may be implemented in a cloud-based environment. It will be understood that the system 102 may be accessed by multiple users through one or more user devices 104-1, 104-2, 104-3, . . . 104-N, collectively referred to as user 104 hereinafter, or applications residing on the user devices 104. Examples of the user devices 104 may include, but are not limited to, a portable computer, a personal digital assistant, a handheld device, and a workstation. The user devices 104 are communicatively coupled to the system 102 through a network 106.

In one implementation, the network 106 may be a wireless network, a wired network, or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 106 may include a variety of network devices, including routers, bridges, servers, computing devices, storage devices, and the like.

Figure 2:
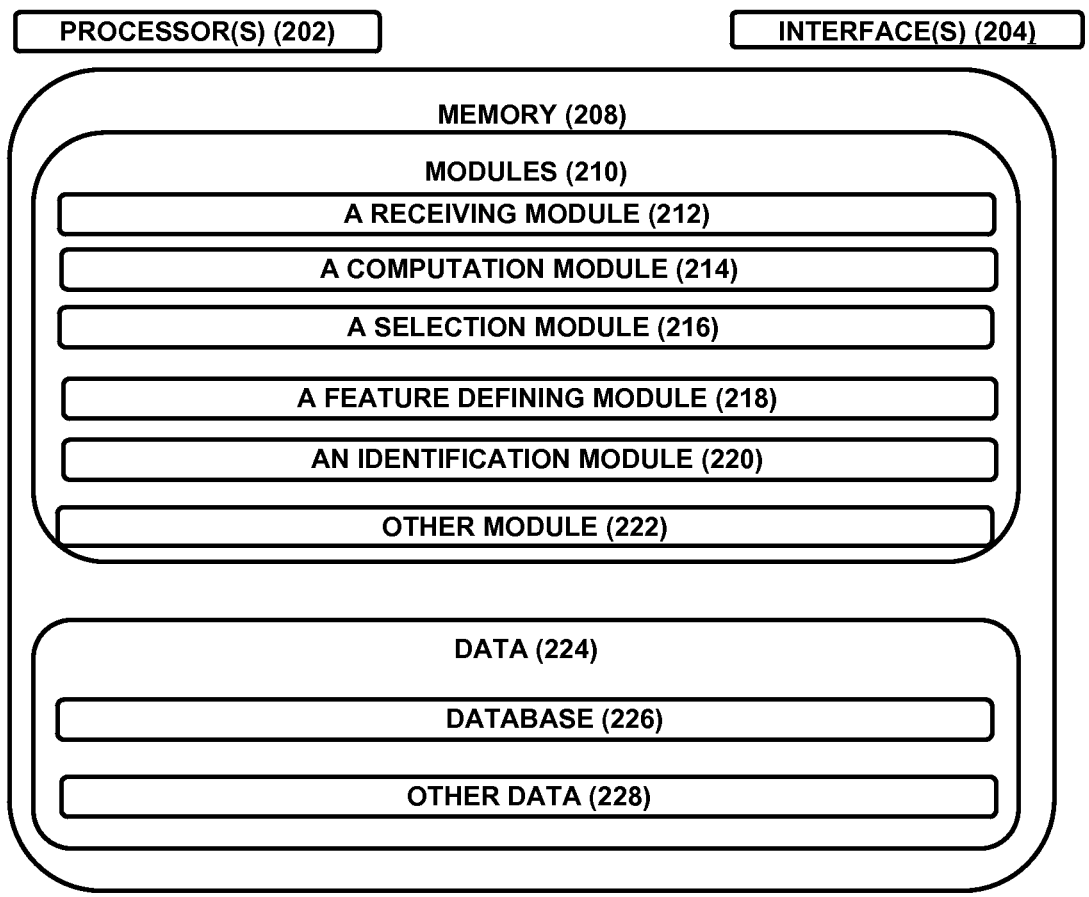
FIG. 2 illustrates the system for selecting features for identifying human activities in a human-computer interacting environment, in accordance with an embodiment of the present subject matter.

Referring now to FIG. 2, the system 102 is illustrated in accordance with an embodiment of the present subject matter. In one embodiment, the system 102 may include at least one processor 202, an input/output (I/O) interface 204, and a non-transitory memory 208. The at least one processor 202 may be implemented as one or more microprocessors, microcomputers, microcontrollers, digital signal processors, central processing units, state machines, logic circuitries, and/or any devices that manipulate signals based on operational instructions. Among other capabilities, the at least one processor 202 is configured to fetch and execute computer-readable instructions stored in the memory 208.

The I/O interface 204 may include a variety of software and hardware interfaces, for example, a web interface, a graphical user interface, and the like. The I/O interface 204 may allow the system 102 to interact with a user directly or through the client devices 104. Further, the I/O interface 204 may enable the system 102 to communicate with other computing devices, such as web servers and external data servers (not shown). The I/O interface 204 can facilitate multiple communications within a wide variety of networks and protocol types, including wired networks, for example, LAN, cable, etc., and wireless networks, such as WLAN, cellular, or satellite. The I/O interface 204 may include one or more ports for connecting a number of devices to one another or to another server.

The memory 208 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 208 may include modules 210 and data 224.

The modules 210 include routines, programs, objects, components, data structures, etc., which perform particular tasks or functions, or which implement particular abstract data types. In one implementation, the modules 210 may include a receiving module 212, a computation module 214, a selection module 216, a feature defining module 218 and an identification module 220. Other modules 222 may include programs or coded instructions that supplement applications and functions of the system 102.

The data 224, amongst other things, serves as a repository for storing data processed, received, and generated by one or more of the modules 210. The data 224 may also include a database 226, and other data 228. The other data 228 may include data generated as a result of the execution of one or more modules in the other module 222.

The present disclosure relates to system(s) and method(s) for selecting features for identifying human activities in a human-computing interaction environment. Out of a plurality of skeleton points (also called as skeleton joints), a set of skeleton points are selected based on a data variation factor. The set of skeleton points is further processed to select one or more features in order to identify the human activities.

Twenty skeleton points are pre-sensed by one or more sensors before processing the skeleton points by the system 102. The one or more sensors comprises of a KINECT® (registered trademark, Microsoft Corporation) sensor. The KINECT® sensor provides geographical coordinates data (XYZ data) for all of the twenty skeleton points.

The twenty skeleton points comprise of Hip Center, Spine, Shoulder Center, Head, Shoulder Left, Elbow Left, Wrist Left, Hand Left, Shoulder Right, Elbow Right, Wrist Right, Hand Right, Hip Left, Knee Left, Ankle Left, Foot Left, Hip Right, Knee Right, Ankle Right, and Foot Right.

The twenty skeleton points are received by the receiving module 212. The twenty skeleton points are associated with the one or more human activities to be identified. The human activities to be identified comprise of standing, sitting, walking, and lying. Out of these activities, sitting and standing are considered to be static activities, whereas walking is considered to be a dynamic activity.

The computation module 214 calculates a data variation factor for each skeleton point. The data variation factor includes a standard deviation value calculated for each skeleton point associated with the human activities. The standard deviation is a measure to compute the variation of the data. The data variation factor (or standard deviation) is indicative of a variation between one or more humans while performing the one or more activity and a variation between one or more human activity.

The natural data (skeleton points) are usually distributed along the mean (average) position. The standard deviation is calculated to find the joint coordinates (skeleton points) that are responsible for accomplishing a particular human activity, from the human activities to be identified.

The data variation factor is calculated to ensure that the skeleton points should not vary a lot from one person to another for a particular action. Similarly, the skeleton points should also vary a lot from one action to another action. The computation module uses a STDEV (standard deviation) as the metric to compute the data variation factor.

The calculation and significance of standard deviation is explained below:

For a particular person performing the same human activity (for example walking or standing), at different times the deviation of the joint positions with respect to time should be at a minimum. The computation module computes the standard deviation as:

$$\sigma_1 = \sqrt{\frac{1}{N}\sum_{i=1}^{N}(x_i - \mu)^2} \text{ where } \mu = \frac{1}{N}\sum_{i=1}^{N}x_i$$

where N is the number of joint positives, $x_i$ the is value of the joint position, and $\mu$ is the mean value of the joint position over N samples.

Therefore, the calculation module 214 computes $\sigma_1$ for each joint position separately for a single person with respect to time, and it should be at a minimum. Ideally, the $\sigma_1$ should be zero for the joints with no noise. If there is huge noise, the joints will oscillate all the time, and if the same joint within some period of time are considered, the variations in the values of $\sigma_1$ are huge.

For different persons performing the same human activity, the standard deviation of the joint positions (skeleton points) should be at a maximum. The computation module 214 calculates standard deviation as:

$$\sigma_2 = \sqrt{\frac{1}{N}\sum_{i=1}^{N}(x_i - \mu)^2} \text{ where } \mu = \frac{1}{N}\sum_{i=1}^{N}x_i$$

where N is the number of joint position values of different persons, $x_i$ is the value of the joint position, and $\mu$ is the mean value of the joint position over N samples. The calculation module 214 computes $\sigma_2$ for each joint position separately for different persons, and it should be at a maximum.

The computation module 214 is further configured to scale both $\sigma_1$ and $\sigma_2$ in between 0 and 1. The scaling is performed by using the below mentioned formula:

$$S = \frac{\sigma - \text{Min}(\sigma)}{\text{MAX}(\sigma) - \text{Min}(\sigma)}$$

Let $S_{\sigma_1}$ and $S_{\sigma_2}$ be the scaled deviations. The scaling is carried out by using above mentioned formula. The scale gives a score between 0 and 1. When $\sigma$ has a max value, then both numerator and denominator will be the same and S=1. When $\sigma$ is having min value then numerator=0 and hence S=0.

And all the $\sigma$ values in between max and min will be within 0 and 1. The scaling function (S) operates in this way. The significance of scaling is to make the joint positions independent of the person—for example, if one person has $\sigma$ values with a min of 2 and a max of 4, and another person has the values min 3 and max 6. Ideally, it should be within same range, but person to person it varies. So, in order to remove this dependency, the standard deviations are scaled to 0 and 1. So, irrespective of the person, the values will always be between 0 and 1.

Once all the standard deviations ($\sigma_1$ and $\sigma_2$) are scaled, it is observed that few skeleton points are scaled with a 0 score. All such skeleton points with a 0 score are redundant. Also, if plotting is done for recognition accuracy over a number of skeleton points, it is further observed that the recognition accuracy for limited skeleton points does not increase after incorporating the top four skeleton points. The top four skeleton points are considered to be the most informative skeleton points (with respect to present disclosure). Therefore, the top four scores given to skeleton points (as per the scale between 0 and 1) are used for the human activity identification.

The computation module 214 is further configured to compute a distance metric for the top five scores, i.e., for the top four scaled standard deviations of the top five joint positions or joint points. The distance metric is represented by:

$$\delta = (1 - S_{\sigma_1}) * S_{\sigma_2}$$

The significance of the distance metric is to choose a reliable joint based on the value of $\delta$. Ideally, $S_{\sigma_1}$ should be at a minimum and $S_{\sigma_2}$ should be at a maximum. As the standard deviations are already scaled, $\delta$ has a minimum value=0 and a maximum value=1. Therefore, if the joints not noisy, then $S_{\sigma_1}=0$ and $S_{\sigma_2}=1$. In this case, the distance metric will be $\delta=1$. If the joint is more noisy then $S_{\sigma_1}=1$ and $S_{\sigma_2}=0$. In this case, the distance metric will be $\delta=0$. Therefore, more reliable joints are the joints for which values of $\delta$ is close to a particular value and the particular value is equal to 1. In this way, Head, Shoulder Center, Shoulder Left and Shoulder Right are chosen based on distance metric as the values of $\delta$ for these joint positions of the joint points is close to 1.

In the next step, the computation module 214 is configured to sort values of the distance metric in a descending order. However, all the values of the distance metrics are close to 1.

With respect to the descending order of the distance metric (so calculated by using the data variation factor), the set of skeleton points is selected by the selection module 216. The set of skeleton points comprises of Head, Shoulder Center, Shoulder Left and Shoulder Right.

After the set of skeleton points are selected, the feature defining module 218 is configured to extract one or more features from the set of skeleton features. The one or more features are extracted from the Head, Shoulder Center, Shoulder Left and Shoulder Right.

The feature defining module 218 is configured to identify a variation in co-ordinates (XYZ data) of the set of skeleton points by using one or more statistical parameters associated with the set of skeleton points. The statistical parameters comprise of a mean, a standard deviation, and a maximum and minimum value of the position co-ordinates (joint positions) of the set of skeleton points associated with the one or more human activities.

The XYZ coordinates of four features are plotted to analyze variation for different activities like standing, sitting, walking, and lying. It is observed that for static activities like standing and sitting, the variation of X and Z is much less as compared to Y, where Y here relates to height. Similarly, it is observed from plotting that variation of X and Z for lying and sitting is very discriminative.

An analysis for checking the variation has been carried out at each frame. It is further observed that most of the time, walking and standing are misclassified. This is mainly due to classifying the activity at frame level. As walking is a dynamic activity therefore, the system 102 considers few frames to discriminate between standing and walking.

The variation in coordinates is identified for different activities like standing, sitting, walking, and lying. The feature defining module 218 identifies that for static activities like standing and sitting, the variation of X and Z is much less as compared to Y (Y gives the height of the human performing the activity) for activities like standing and sitting. The identification module further identifies that the variation of X and Z for lying and sitting is very discriminative. Based on the variation in coordinates identified by the feature defining module 218, it is further identified that in most cases, walking and standing are misclassified. This happens mainly due to classification of human activity at frame level.

As walking is a dynamic human activity, identification of a variation in coordinates is performed by the feature defining module 218 at few frames, to discriminate between standing and walking. The few frames comprises of thirty frames (approximately 1 second of data).

The statistical parameters (mean, standard deviation, and a maximum and minimum value of co-ordinates of the set of skeleton points) shows that if the human is walking towards the sensor)(KINECT®), there is variation in Z co-ordinate. And if the human is walking towards the left and the right of the sensor (KINECT®) there is a variation in the X coordinate. The feature defining module 218 identifies the variation by taking the mean values of the coordinates of the skeleton points for every thirty frames.

The feature defining module 218, while identifying the variation in coordinates, further identifies that the maximum and minimum values of the coordinates for standing and walking also vary due to the dynamics of the joints in a walking activity. However, for static activities (sitting and lying), the variation of the max and min values of the joints is not much. Therefore, the feature defining module 218 selects the features by considering a range using the difference between the max and min values of the joint positions to discriminate static and dynamic activities.

The feature defining module 218 is further configured to extract the one or more features based on the variation or change in position coordinates of the set of skeleton points.

The one or more features comprises a mean of the set of skeleton points and a difference between the maximum and minimum (i.e. range) of joint positions (position coordinates) associated with human activities. The difference between the maximum and minimum values of the joint positions comes out to be a constant for static activities, and the difference between the maximum and minimum values of the joint points comes out to be a numeric value (not constant) for dynamic activities. Therefore, the feature defining module 218 uses the difference between the maximum and minimum values of the joint position as the feature for identifying activities. For example, when a person is walking in front of a sensor, there is a change in the Z axis value out of the three coordinates. And the difference between the maximum and minimum values of the joint position comes out to be close to a numeric constant. Further, a person may have small movements while sitting and standing. However, the feature (max-min) will have large value for walking (a dynamic activity), as compared to a small value (due to small moments in a static activity like sitting). Hence, the difference between the maximum and minimum of the joint positions may be considered as the feature for identifying the walking activity.

The feature selection module extracts $F_{mean}F_{max-min}$ as two features with 12 attributes {3 (coordinates)×4 (joints)} extracted for every 30 frames.

Figure 4:
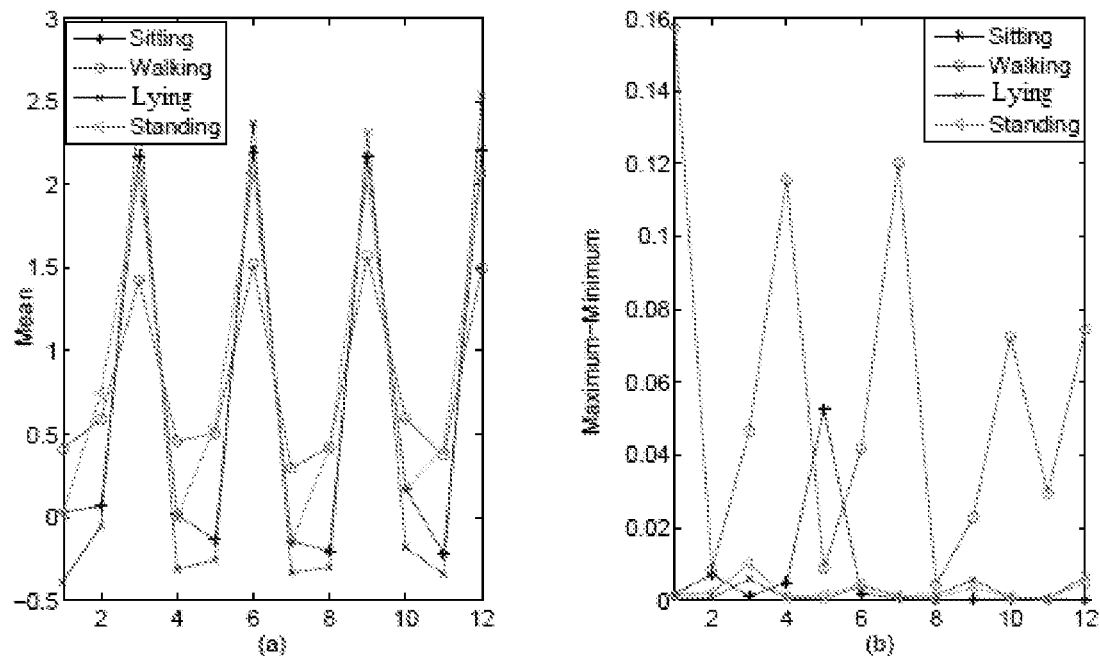
FIG. 4 shows results of identifying human activities by using the features defined by the system in accordance with an embodiment of the present subject matter.

The identification module is configured to identify the human activity by using the one or more features. The identification module executes a Support Vector Machine (SVM) learning algorithm over the one or more features in order to identify the human activity. The SVM is explored as a machine learning tool with 5-fold cross validation, with 4:1 for training and testing. FIG. 4 shows results of features so selected for a set of skeleton joints (4 skeleton joints) for the corresponding four activities (sitting, walking, lying, and standing).

Table 1 shows the average classification of performance of features for identifying human activities.

| Serial No | Features | Average classification performance (%) |
|---|---|---|
| 1 | Maximum-minimum of joint positions | 86.32 |
| 2 | Mean | 89.93 |
| 3 | Combination of 4 and 5 | 94.06 |

Figure 5:
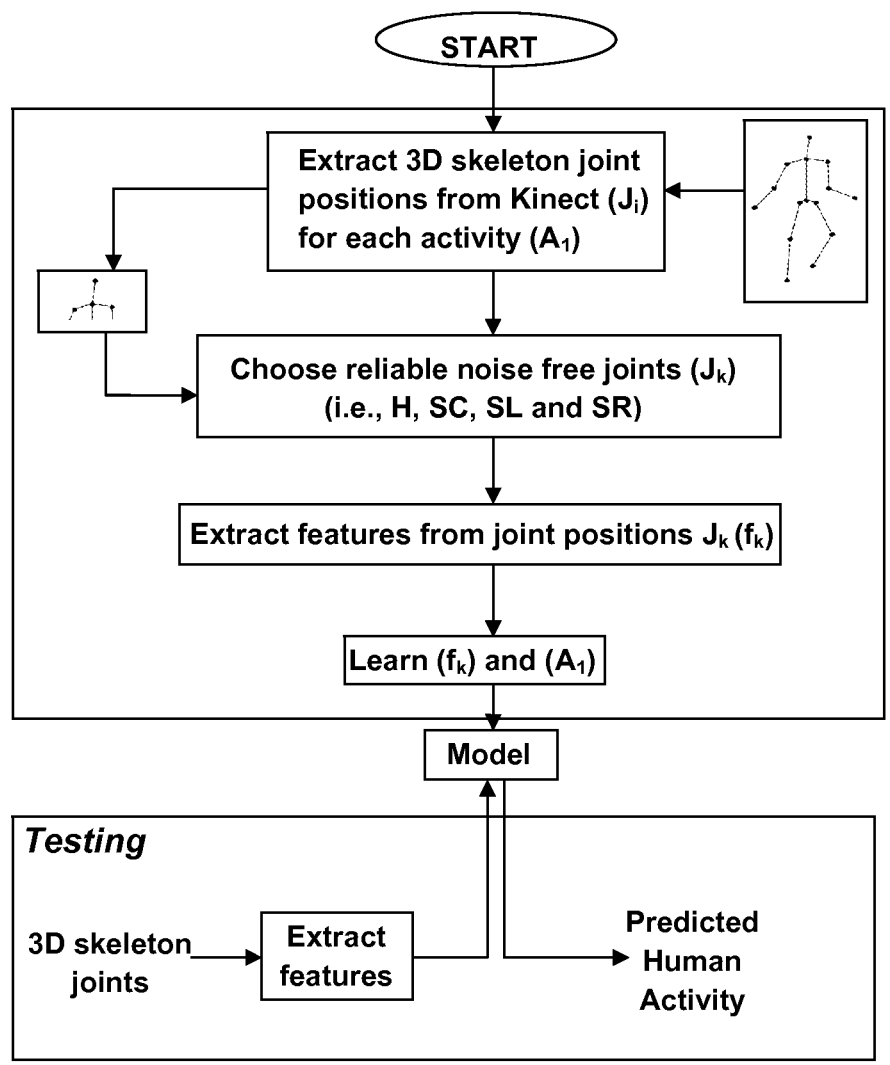
FIG. 5 illustrates system architecture for identifying human activities accordance with an embodiment of the present subject matter.

Referring to FIG. 5, architecture for identifying human activities in a human-computing interacting environment is illustrated. Skeleton points (3D skeleton joint positions) are sensed by the sensor (Kinect $J_i$) for each activity $A_i$ (Standing, walking, lying, and sitting) are received by the receiving module 112. A set of skeleton points are selected. The set of skeleton points are referred to as reliable noise-free joints ($J_k$), i.e., (Head, Shoulder Center, Shoulder Left, and Shoulder Right). Features are extracted from the joint positions $J_k(f_k)$. By using the SVM learning algorithm, testing is performed, i.e., human activities are identified.

The SVM is used to discriminate activities. SVM classification is an example of supervised learning. SVMs are useful due to their wide applicability for classification tasks in many classification problems. A classification task usually involves training and testing data which consist of some data instances. In the training set, each instance contains one target class label and many attributes. The main goal of SVM for a classification problem is to produce a model which predicts a target class label of data instances in the testing set, given only the attributes. The SVM models for different activities were developed as a one-against-rest principle. The SVM model for the specific activity was developed, by using feature vectors derived from the desired activity as positive examples and the feature vectors derived from the other activities as negative examples. A radial basis function (RBF) kernel, unlike a linear kernel, is used by the system 102 to map the data points to higher dimensional space, as it can handle the case where the relation between the class labels and the attributes is nonlinear. The reason to use RBF kernel function is due to its universal approximation properties.

Figure 3:
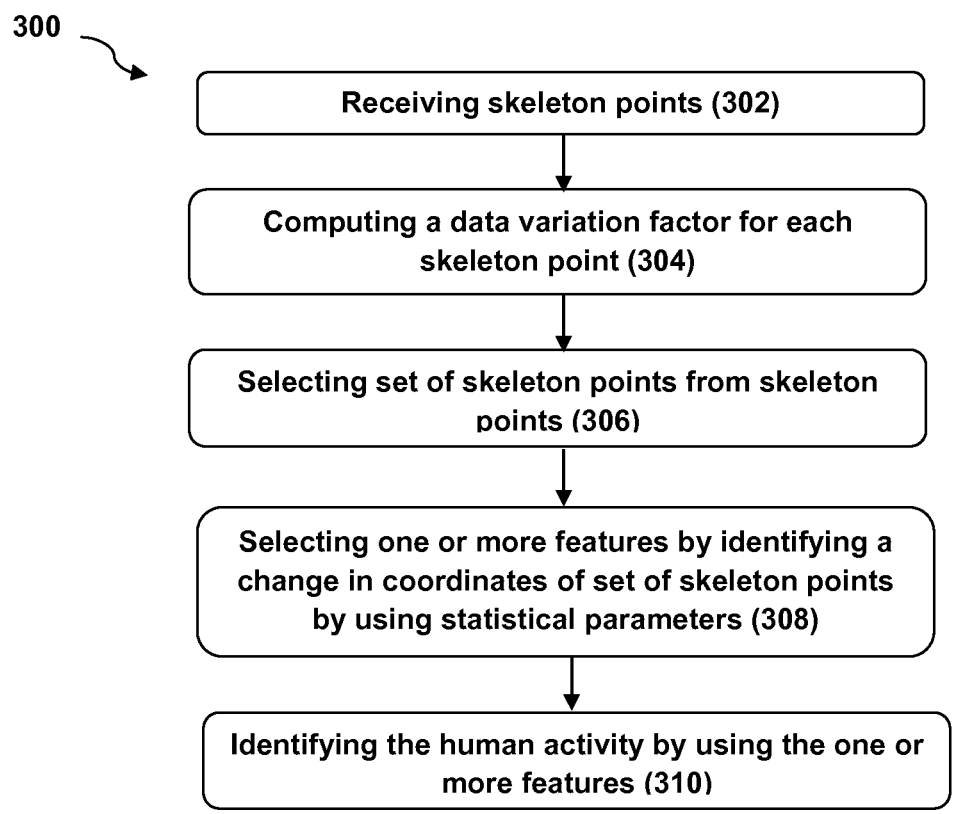
FIG. 3 illustrates a method for selecting features for identifying human activities in a human-computer interacting environment, accordance with an embodiment of the present subject matter.

Referring to FIG. 3, the order in which the method 300 is described is not intended to be construed as a limitation, and any number of the described method blocks can be combined in any order to implement the method 300 or alternate methods. Additionally, individual blocks may be deleted from the method 300 without departing from the spirit and scope of the subject matter described herein. Furthermore, the method can be implemented in any suitable hardware, software, firmware, or combination thereof. However, for ease of explanation, in the embodiments described below, the method 300 may be considered to be implemented in the above described system 102.

At block 302, skeleton points associated with the one or more human performing human activities to be identified are received.

At block 304, a data variation factor for each skeleton point is calculated.

At block 306, set of skeleton points is selected based on the data variation factor.

At block 308, one or more features are defined with respect to change in position coordinates of the set of skeleton points by using statistical parameters.

At block 310, human activities are identified by using the one or more features.

The written description describes the subject matter herein to enable any person skilled in the art to make and use the embodiments of the invention. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

We claim:

1. A system for selecting one or more features to identify one or more human activities in a human-computer interacting environment, the system comprising:
   a processor;
   a non-transitory memory coupled to the processor, wherein the processor is capable of executing a plurality of modules stored in the memory, and wherein the plurality of modules comprise:
      a receiving module that receives skeleton points associated with one or more humans, wherein the one or more humans perform the one or more human activities, and wherein the skeleton points comprise a plurality of position coordinates of the one or more humans;
      a computation module that:
         calculates a data variation factor for the skeleton points, wherein the data variation factor identifies a variation between two or more of the plurality of position coordinates of the one or more human, and wherein the data variation factor is indicative of a variation between the one or more humans performing one or more activities and a variation between the one or more human activities;
         scales the data variation factor with respect to a maximum and a minimum value and sorts the data variation factor by distance metrics in a descending order such that the skeleton point is independent of the one or more human; and
         computes the distance metrics by scaling first four maximum values, wherein first four maximum values correspond to five position coordinates from amongst the plurality of position coordinates;
      a selection module that selects a set of skeleton points from the skeleton points based on the scaled data variation factor;
      a feature defining module that:
         identifies a change in position coordinates associated with the set of skeleton points by using one or more statistical parameters, wherein the set of skeleton points defines the one or more human activity to be identified; and
         extracts one or more features from the set of skeleton points based on the change in the position coordinates; and
      an identification module to identify the one or more human activities based on the extracted one or more features.

2. The system of claim 1, wherein the skeleton points comprise 20 skeleton joints, wherein the 20 skeleton joints comprise a Hip Center, a Spine, a Shoulder Center, a Head, a Shoulder Left, an Elbow Left, a Wrist Left, a Hand Left, a Shoulder Right, an Elbow Right, a Wrist Right, a Hand Right, a Hip Left, a Knee Left, an Ankle Left, a Foot Left, a Hip Right, a Knee Right, an Ankle Right, and a Foot Right.

3. The system of claim 1, wherein the one or more human activities comprises standing, sitting, walking, and lying.

4. The system of claim 1, wherein the selection module selects data variation factors close to a particular value of the distance metrics, wherein the particular value includes a value equal to 1.

5. The system of claim 1, wherein the computation module calculates the data variation factor based on a standard deviation value for the skeleton points.

6. The system of claim 1, wherein the set of skeleton points comprise a Head, a Shoulder Center, a Shoulder Left, and a Shoulder Right.

7. The system of claim 1, wherein the identification module executes a Support Vector Machine (SVM) learning algorithm over the one or more features to identify the one or more human activities.

8. The system of claim 1, wherein the one or more statistical parameters comprise a mean, a standard deviation, and a maximum and a minimum position coordinates of the set of skeleton points associated with the one or more human activities.

9. The system of claim 1, wherein the variation between two or more of the plurality of position coordinates of the set of skeleton points is identified for a period of 30 frames.

10. The system of claim 1, wherein the one or more features comprises a mean of the set of skeleton points and a difference between a maximum and a minimum of the plurality of position coordinates associated with the one or more human activities.

11. A method for selecting one or more features to identify one or more human activities in a human-computer interacting environment, the method comprising:

receiving skeleton points associated with one or more humans, wherein the one or more humans performs the one or more human activities, and wherein the skeleton points comprise position coordinates of the one or more human;

calculating a data variation factor for the skeleton points, wherein the data variation factor identifies a variation between the position coordinates of the one or more humans and wherein the data variation factor is indicative of a variation between the one or more humans performing one or more activities and a variation between the one or more human activities;

scaling the data variation factor with respect to a maximum and a minimum value and sorts the data variation factor by distance metrics in a descending order such that the skeleton point is independent of the one or more human;

computing the distance metrics by scaling first four maximum values, wherein first four maximum values correspond to five position coordinates from amongst the plurality of position coordinates;

selecting a set of skeleton points from the skeleton points based on the scaled data variation factor;

identifying a change in position coordinates associated with the set of skeleton points by using one or more statistical parameters, wherein the set of skeleton points defines one or more human activity to be identified;

extracting one or more features from the set of skeleton points based on the change in the position coordinates; and identifying the one or more human activities by using the extracted one or more features.

12. The method of claim 11, wherein the one or more human activities is identified by executing a Support Vector Machine (SVM) learning algorithm over the one or more features.

13. A non-transitory computer storage medium having embodied thereon a computer program for selecting one or more features to identify one or more human activities in a human-computer interacting environment, the method comprising:

a program code for receiving skeleton points associated with one or more humans, wherein the one or more humans performs the one or more human activities, and wherein the skeleton points comprise position coordinates of the one or more human;

a program code for calculating a data variation factor for the skeleton points, wherein the data variation factor identifies a variation between the position coordinates of one or more humans, and wherein the data variation factor is indicative of a variation between the one or more humans performing one or more activities and a variation between the one or more human activities;

a program code for scaling the data variation factor with respect to a maximum and a minimum value and sorts the data variation factor by distance metrics in a descending order such that the skeleton point is independent of the one or more human;

a program code for computing the distance metrics by scaling first four maximum values, wherein first four maximum values correspond to five position coordinates from amongst the plurality of position coordinates;

a program code for selecting a set of skeleton points from the skeleton points based on the scaled data variation factor;

a program code for identifying a change in the position coordinates associated with the set of skeleton points by using one or more statistical parameters, wherein the set of skeleton points defines the one or more human activities to be identified;

a program code for extracting one or more features from the set of skeleton points based on the change in the position coordinates; and a program code for identifying the one or more human activities by using the extracted one or more features.

* * * * *